(12) United States Patent
Munn

(10) Patent No.: US 10,738,446 B1
(45) Date of Patent: Aug. 11, 2020

(54) DRAIN DISINFECTING DEVICE AND METHOD OF INSTALLING THE SAME

(71) Applicant: STERILUMEN, INC., Tarrytown, NY (US)

(72) Inventor: Max Munn, Tarrytown, NY (US)

(73) Assignee: SteriLumen, Inc., Tarrytown, NY (US)

( * ) Notice: Subject to any disclaimer, the term of this patent is extended or adjusted under 35 U.S.C. 154(b) by 0 days.

(21) Appl. No.: 16/538,296

(22) Filed: Aug. 12, 2019

(51) Int. Cl.
  *A61L 2/24* (2006.01)
  *A61L 2/10* (2006.01)
  *E03C 1/126* (2006.01)

(52) U.S. Cl.
  CPC .............. *E03C 1/126* (2013.01); *A61L 2/10* (2013.01); *A61L 2/24* (2013.01); *A61L 2202/11* (2013.01); *A61L 2202/14* (2013.01)

(58) Field of Classification Search
  CPC ... E03C 1/126; A61L 2/24; A61L 2/10; A61L 2202/11; A61L 2202/14
  See application file for complete search history.

(56) References Cited

U.S. PATENT DOCUMENTS

| | | | |
|---|---|---|---|
| 3,953,059 A * | 4/1976 | Carroll | F16L 47/20 285/192 |
| 5,225,083 A | 7/1993 | Pappas et al. | |
| 6,666,966 B1 | 12/2003 | Schluttig | |
| 6,838,400 B1 * | 1/2005 | Japp | B32B 5/26 428/417 |
| 2005/0135979 A1 | 6/2005 | Gootter | |
| 2008/0213128 A1 * | 9/2008 | Rudy | A61L 2/10 422/24 |
| 2010/0237254 A1 * | 9/2010 | Mason | A61L 2/10 250/435 |
| 2011/0008205 A1 | 1/2011 | Mangiardi | |
| 2013/0146783 A1 * | 6/2013 | Boodaghians | C02F 1/325 250/435 |
| 2013/0206187 A1 * | 8/2013 | Dombrowski | B08B 3/04 134/169 R |
| 2013/0233511 A1 * | 9/2013 | Swedberg | F21V 27/02 165/80.2 |

(Continued)

FOREIGN PATENT DOCUMENTS

| | | |
|---|---|---|
| CN | 109811837 A | 5/2019 |
| JP | 2001095699 A | 4/2001 |

(Continued)

*Primary Examiner* — Brooke Purinton
(74) *Attorney, Agent, or Firm* — Myron Greenspan Lackenbach Siegel LLP

(57) ABSTRACT

A drain disinfecting device for disinfecting the internal surface of a drain pipe wall that is provided with a hole or aperture includes a UV LED module provided with a transparent lens through which UV-C light can be transmitted. The module is attached to the drain pipe to register the transparent lens with the hole in the drain pipe to transmit UV light through the transparent lens into the interior of the drain pipe to irradiate the drain pipe inner surface with UV light. A watertight seal is provided between the drain pipe and the module. A controller is provided for selectively energizing the module. A method of converting an existing drain pipe to disinfect the interior surface includes forming a hole or aperture in the wall of the drain pipe and registering the drain disinfecting device with the hole or aperture in the drain pipe.

18 Claims, 3 Drawing Sheets

(56) References Cited

U.S. PATENT DOCUMENTS

| | | | |
|---|---|---|---|
| 2013/0236353 A1* | 9/2013 | Blechschmidt | A61L 9/20 422/4 |
| 2016/0271280 A1* | 9/2016 | Liao | A61L 2/10 |
| 2017/0314243 A1* | 11/2017 | Koll | A61L 2/10 |
| 2018/0291602 A1* | 10/2018 | Schluttig | E03C 1/126 |
| 2019/0142981 A1 | 5/2019 | Kim et al. | |

FOREIGN PATENT DOCUMENTS

| | | |
|---|---|---|
| JP | 2001112855 A | 4/2001 |
| JP | 2010275840 | 12/2010 |
| JP | 2010275841 | 12/2010 |
| JP | 2013185308 | 9/2013 |
| KR | 101410192 | 6/2014 |
| KR | 101784210 | 10/2016 |
| KR | 20180002069 | 1/2018 |
| KR | 20180096040 | 8/2018 |
| KR | 101905518 | 10/2018 |
| WO | 2002081829 A1 | 10/2002 |
| WO | 2011032543 A3 | 3/2011 |
| WO | 2019043062 A1 | 3/2019 |

\* cited by examiner

DRAIN DISINFECTING DEVICE AND METHOD OF INSTALLING THE SAME

BACKGROUND OF THE INVENTION

1. Field of the Invention

This invention generally relates to controlling levels of bacteria in sink installations and, more specifically, to a drain disinfecting device and method of installing the same.

2. Description of the Background Art

High levels of moisture in a sink drain pipe create perfect conditions for numerous bacteria and other pathogens to grow and thrive. Also, because organic products and other nutrients are frequently disposed of in hospital sinks and kitchen sinks the drain pipes for these sinks contain extensive levels of bacteria. Disposing hair, soap and dead skin down the sink doesn't just cause blockages, but can also provide the environment for a deadly threat.

Drain pipes between the sink basin and the P-trap or U-trap are ideal for pathogen growth. The inside surfaces of such drain pipes are typically warm, moist and contain nutrients that pathogens can feed on, enabling them to thrive. Bacteria that are health hazard include *salmonella* that can be fatal with those with compromised immune systems and *E. coli* that can be life-threatening but usually only results in diarrhea, *Fusarium solani* that can lead to permanent vision damage and many more pathogens that can cause urinary tract infections and other illnesses.

When unattended, micro-organisms including virus, bacteria, fungi, diatoms and algae stick together and form biofilms. Micro-organisms like to grow on moist, nutrient-rich surfaces, especially in the presence of bathroom blockages caused by hair, soap, sulfates and oils. Once fully formed, biofilms are notoriously difficult to get rid of as they become immune to antibiotics contained in cleaning agents. In hospitals, where liquids or fluids are commonly poured into hospital sinks, such as unused intravenous fluids and left over beverages, pathogens flourish when they multiply to create biofilms. A film can rise up along the inner surface of a pipe at a rate of 2.5 cm (approximately 1") per day to contaminate sink drain covers. Once a biofilm reaches a sink strainer or inlet it can instantly be spread from the strainer to the countertop surrounding the sink, from where it could be potentially distributed further, either by individuals touching the surface or objects placed upon it. At that point, even clean faucet water can splatter the bacteria and other pathogens around the sink bowl and countertop. With only one sink contaminated, running water even with no nutrients, may be enough for the bacteria to infiltrate other sinks through a common drain pipe and an interconnected plumbing system in just one week.

The micro-organisms that grow inside drain pipes can be varied and dangerous to people when exposed to them, and particularly to those individuals that have lowered or weakened immune systems. Some people only need to be exposed to as little 1 mg or less of *Staphylococcus aureus* to lead to staff-related illness and infection. See, for example, "Microbial Characterization of Biofilms in Domestic Drains and the Establishment of Stable BioFilm Microcosms" McBain et al, Applied and Environmental Microbiology, January 2003, 69(1): 177-185.

A number of solutions have been proposed to control the growth of micro-organisms in drain pipes. In Korean Publication KR2016/6083569A a sterilizing and deodorizing apparatus is disclosed that uses a series of UV LEDS arranged along the inside surface of the actual drain pipe and enclosed within a cylindrical quartz protective cover projecting into the drain pipe, thereby narrowing the drain pipe passageway. The sterilizing and deodorizing apparatus is an OEM product and not suitable for after market installations into existing sinks. In Japanese Publication JP05291487B2 UV LEDS are incorporated within a drainage portion of the sink. The UV LEDs are mounted directly within the drainage portion. The installation provides a hygienic equipment chamber, and is also suitable for OEM installations. Therefore, this device is, likewise, not suitable for use with existing sink fixtures. Another OEM-style product is disclosed in Korean Publication KR2017/0022190A for a sink with ultra-violet ray sterilization function. The disclosed device includes a cover panel as part of a kitchen appliance. The cover panel is transparent and a source of UV is placed below the panel so that kitchen tools, dish towels, kitchen utensils and the like can be placed on top of the cover panel to expose them to the ultra-violet lamp. Japanese Publication JP5945135B2 discloses a drainage part of a sink. A coating layer of a photocatalyst is applied to the inner surface of the drain cylinder. An LED light source is positioned at the inlet to the drain pipe for transmitting UV through a transparent wall to which an externally positioned LED light source is attached, introducing UV radiation upstream of the drain pipe to promote the decomposition and removal of dirt stuck to the inner surface of the drain cylinder.

The aforementioned devices, as indicated, are primarily for OEM installations or special purpose sink basins, focusing on one region of the sink basin or proximate portion of a drain pipe and do not address the buildup of pathogens along the downstream ends of drain pipes leading up to the traps where micro-organisms can and normally do flourish.

SUMMARY OF THE INVENTION

Accordingly, it is an object of the present invention to provide a drain disinfecting device that does not have the disadvantages of prior art devices.

It is another object of the invention to provide a drain disinfecting device that is easily installed with any new or existing sink drain pipe installation.

It is still another object of the invention to provide a drain disinfecting device as in the previous objects that is simple in construction and economical to manufacture.

It is yet another object of the invention to provide a drain disinfecting device that can be configured and flexibly positioned along a drain pipe to expose most or all of the internal surfaces of drain pipes.

It is a further object of the invention to provide a drain disinfecting device that is effective in eliminating most pathogens that normally proliferate in drain pipes.

It is still a further object of the invention to provide a method for easily, quickly and inexpensively installing a drain disinfecting device in accordance with the invention without the need for specialized sink basins or specialized tools.

It is yet a further object to provide a drain disinfecting device and method of installing the same that enables two or more such devices to be installed along the length of a drain pipe to enhance or maximize elimination of pathogens along all or substantial position of the drain pipe.

The above objects, and others that will become apparent hereinafter, are obtained with a drain disinfecting device in accordance with the invention. The drain disinfecting device, used for disinfecting the internal surface of a drain pipe wall provided with a hole or aperture, comprises a UV LED module provided with a transparent medium through which UV light can be transmitted. Said module is attached to the drain pipe to register said transparent medium with the hole in the drain pipe to transmit UV light through said transparent medium into the interior of the drain pipe to irradiate the drain pipe inner surface with UV light. A seal is used to create a water-tight seal between the drain pipe and the module. Control means is used to selectively energize said module.

A modified drain pipe for use between a sink basin and a trap comprises an integrated drain disinfecting device for disinfecting the internal surface of the drain pipe wall through a hole or aperture in the drain pipe. Said drain disinfecting device comprises a UV-C LED module provided with a transparent waterproof lens through which UV-C light can be transmitted. Said module is integrated with the drain pipe to transmit UVC light through said transparent waterproof lens into the interior of the drain pipe to irradiate the drain pipe inner surface with UVC light. Sealing means is provided for creating a water tight seal between the drain pipe and said module. The modified drain pipe is connected to means for energizing said module.

A method of converting a drain pipe to disinfect the interior surface thereof comprises the steps of forming a hole or aperture in a wall of the drain pipe. A drain disinfecting device, comprising a UV-C LED module, is positioned to register a transparent portion of the device with said hole or aperture in the drain pipe to enable UV-C light to be transmitted into the drain pipe through the hole or aperture. Said module is sealingly secured to the drain pipe to enable UV-C light to irradiate the drain pipe inner surface while creating a water tight seal to prevent fluid from escaping from the drain pipe.

BRIEF DESCRIPTION OF THE DRAWINGS

Those skilled in the art will appreciate the improvements and advantages that derive from the present invention upon reading the following detailed description, claims, and drawings, in which:

DETAILED DESCRIPTION

Figure 1:
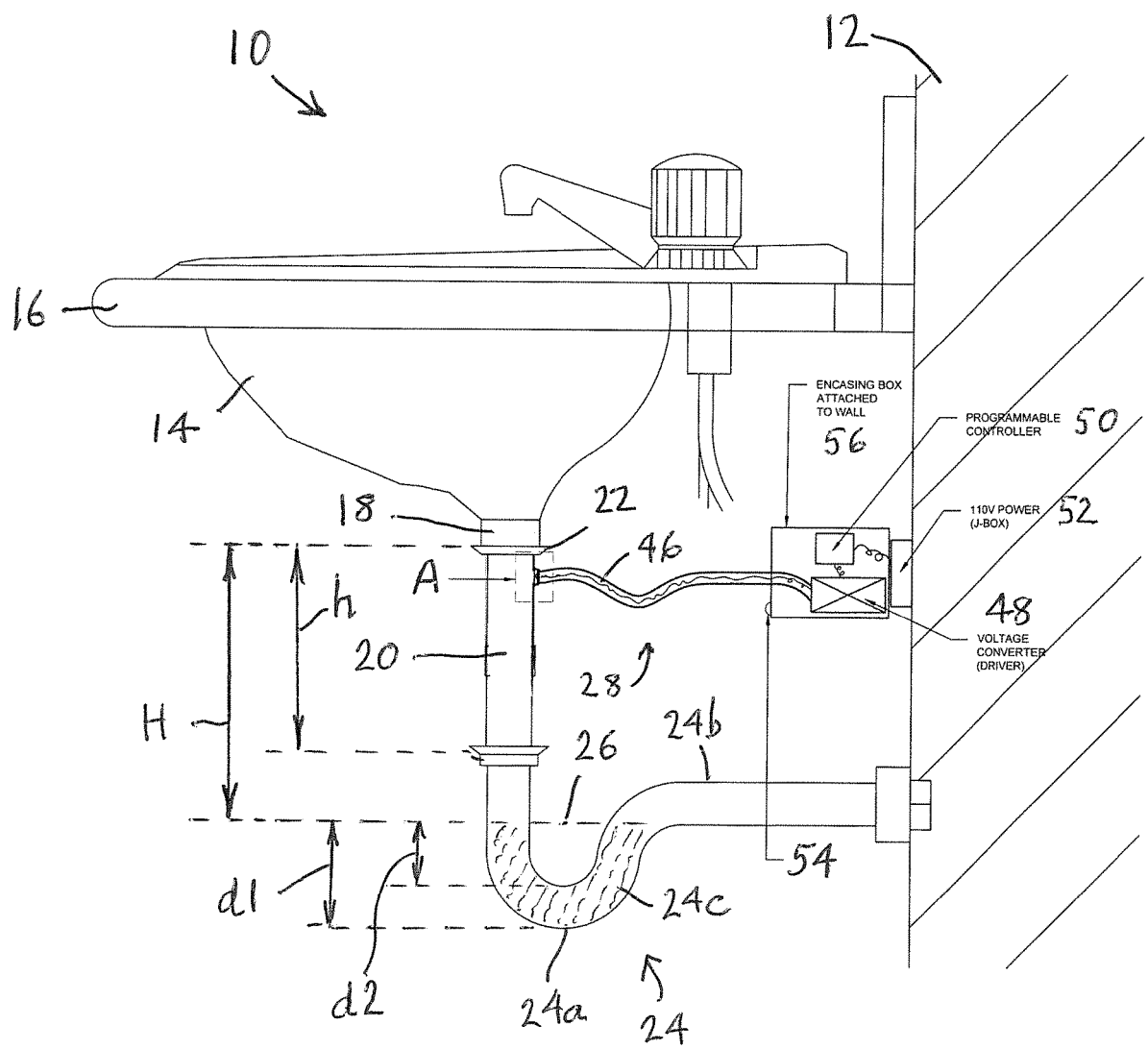
FIG. 1 is a diagrammatic representation of a sink installation, showing how a drain disinfecting device in accordance with the invention can be installed to disinfect the internal surface of the pipe wall.

Referring now specifically to the drawings, in which the identical or similar parts are designated by the same reference numerals throughout, a sink installation is generally designated by the reference numeral 10.

The sink installation 10 can represent a sink, for example, in a bathroom or in a kitchen or elsewhere. As shown, the sink installation is typically mounted on a wall 12, with the sink basin 14 supported on a countertop or support panel 16 and, as with most sink basins, is provided with a fixture tail piece 18 designed to be connected to a drain pipe.

While many different drain pipe configurations are used in connection with different sinks, a simple arrangement is illustrated in FIG. 1 in which the tail piece 18 is joined to a drain pipe 20 by means of a union or a locknut 22. The drain pipe 20, in turn, is connected to an outlet pipe 24 by means of another union or locknut 22 as shown. The outlet pipe 24, sometimes referred as a P-pipe or tube, includes a U-shaped trap 24a and a horizontal extension portion 24b through which waste water is drained to a sewer pipe. Under normal conditions, without blockages, air locks or other pressure differentials, U shaped traps are filled with waste water 24c to a level determined by the overflow level 26. When water rises above the overflow level 26 it flows out through the horizontal extension 24b to the main waste pipes. The regions of the drain pipe that are normally problematic in terms of organism proliferation are designated by the height "H". This region, as suggested, is exposed to moisture, air or oxygen as well as nutrients that are flushed down the drain. The level of the liquid "d1" within the U-shaped trap 24a prevents gases from the sewer pipes entering the space where the sink installation is located through the sink basin. The level "d2" is normally referred to as the trap seal depth and can range between 1.5-4" to ensure that there is no reverse flow of noxious gases. The invention is designed to provide UV-C light that irradiates most or all of the drain pipe 20 over the height h and, preferably, along the entire height H.

In FIG. 1 a drain disinfecting device in accordance with the invention is generally designated by the reference numeral 28. The device 28 includes a UV-C LED module 30 (FIG. 2) that includes an enclosure 32. The drain pipe 20 is provided with a hole, aperture or opening 34 in its wall. The LED module includes a housing 36 with a UV-C LED 38 mounted therein. A quartz or other water proof lens 40 is provided, the lens 40 forming a transparent medium through which UV light can be transmitted.

The enclosure 32 can be secured to the side of the drain pipe 20 in any conventional manner and is positioned to register the transparent medium or lens 40 with the hole or aperture 34 in the drain pipe to transmit UV light through the transparent medium into the interior drain pipe in order to irradiate the inner surface of the drain pipe with UV light. To ensure that there is no leakage when water is being flushed down the drain any suitable seal 42 is provided for creating a water tight seal between the seal and the module. While UV light having different peaks may be used UV-C is preferred as a single source of UV light.

Figure 2:
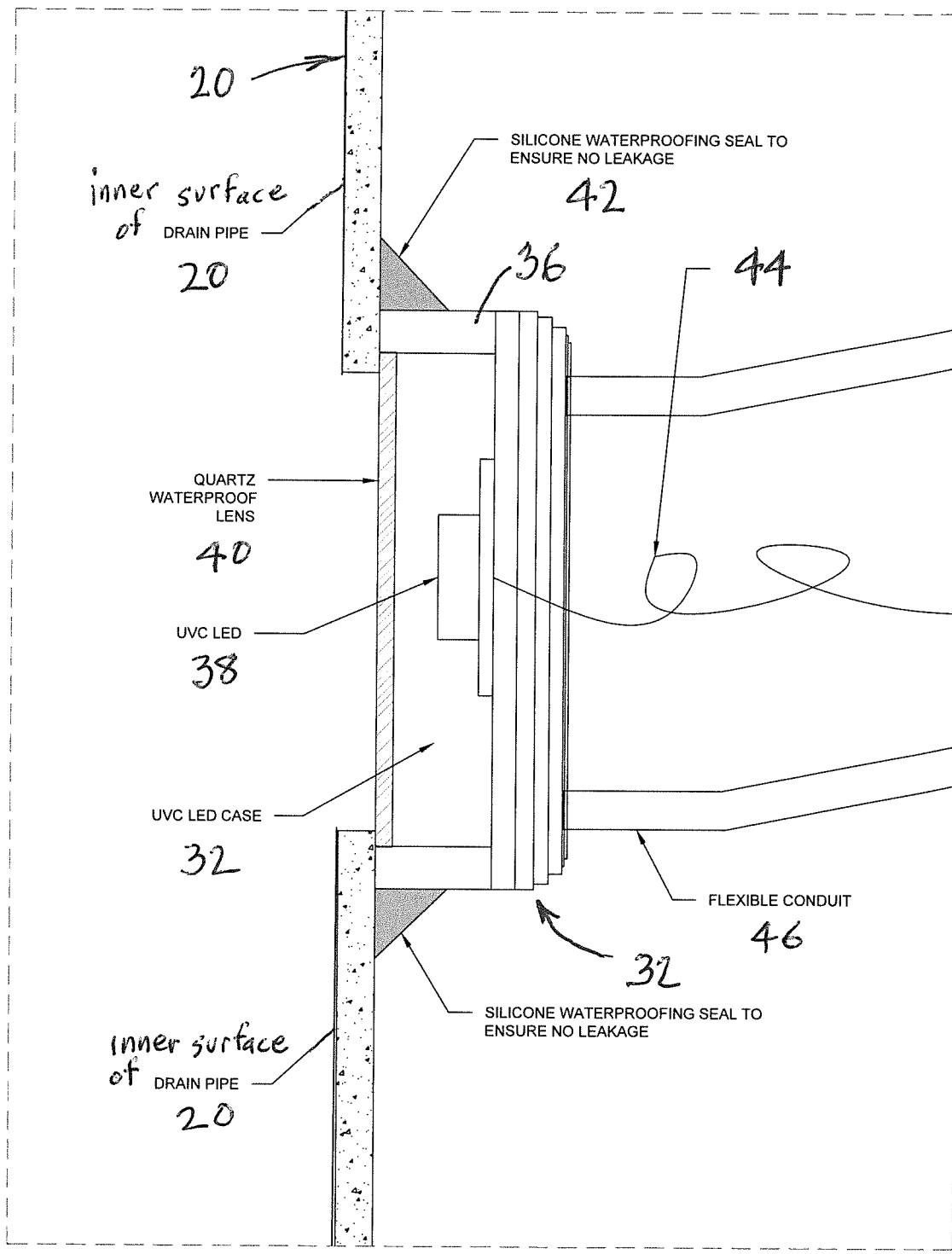
FIG. 2 is an enlarged detail of region A in FIG. 1 showing how a UV-C LED module is secured and interacts with the drain pipe.

While the lens 40 is preferably made of quartz, any suitable glass or transparent material may be used. In FIG. 2, the seal 42 is in the form of silicone adhesive.

The UV-C LED 38 is connected by means of electrical conductors 44 within a conduit 46 to a suitable voltage converter 38 that serves as a driver for the LED. The driver 48 is connected to a programmable controller 50 which, in turn, is connected to a source of power, such as a 110 volt power outlet at a J-box 52. The programmable controller 50 is also advantageously connected to a motion detector 54 that can detect motion in the general facility or area of the sink basin. The programmable controller 50 and the voltage converter or driver 48 are preferably enclosed within a box or housing 56 that can be attached to the wall 12. The enclosure 56 is also advantageously water resistant. To facilitate installation, the conduit 46 is preferably a flexible conduit that can be extended between and connected to the casing enclosure 56 and the drain pipe 20.

Figure 3:
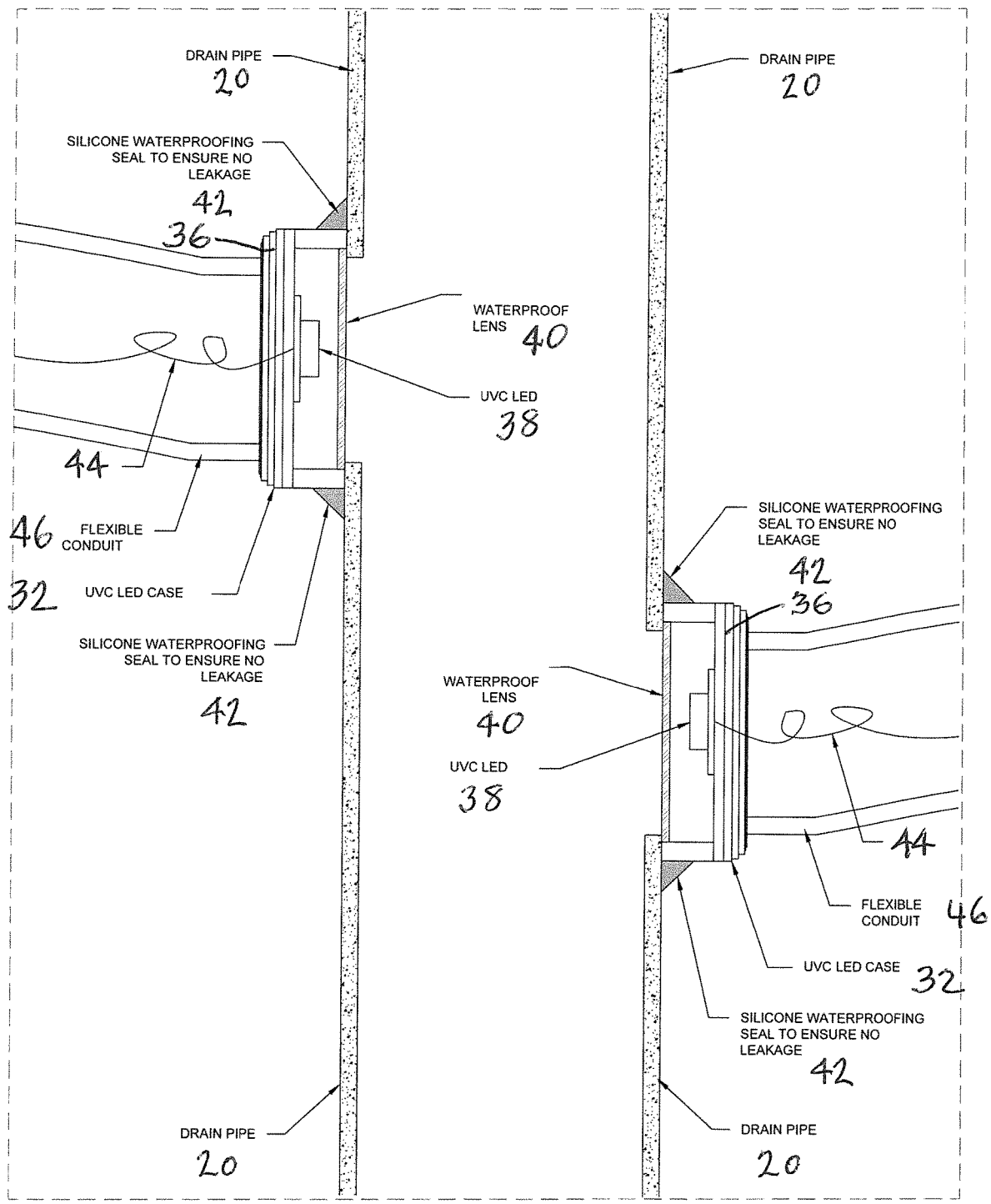
FIG. 3 is similar to FIG. 2 but shows 2 modules installed on a single drain pipe, the modules being linearly and angularly spaced or offset from each other in relation to the axis or length direction of the drain pipe.

In FIGS. 1 and 2 only one module is shown. It will be appreciated that two or more modules may also be installed on a single drain pipe, as shown in FIG. 3. When two or more UV-C LED modules are used they are preferably linearly and angularly spaced or offset from each other in relation to the axis or length direction of the tail pipe 20 to maximize the surface area exposed to the UVC radiation.

In FIGS. 2 and 3, the lenses 40 are generally flat and abut against the outside surface of the drain pipe to prevent interference with the normal flow of waste water down the drain. However, a greater drain pipe inner surface area exposed to radiation may be obtained by utilizing a spherical or conical surface lens that slightly projects into the interior of the drain pipe. This allows the UV-C LED to be moved closer to the center of the drain pipe, as suggested by the dash outlines in FIG. 2. However, such extension of the module into the drain pipe should normally not exceed ¼ of an inch to insure the normal flow and operation of the drain pipe.

Installation of the devices shown in FIGS. 1-3, by adding the UV-C LED modules to existing drain pipe installations, requires the installer to drill or otherwise create one or more openings or holes 34.

The invention also contemplates a modified drain pipe 20 that is manufactured with the UV-C module already integrated with the drain pipe to eliminate the drilling step. A modified drain pipe can be produced in standard lengths. A plumber or other installer can simply cut off a tail end of the pipe as needed, to fit a particular installation or plumbing arrangement below the sink basin. In this case, the drain pipe with the integrated module only needs to be connected to the tail piece 18 of the sink basin and to the outlet pipe 24. In such case, the installation only requires an electrical connection to be made between the conductors 44 within the conduit 46 and the voltage converter or driver 48 within the box or housing 56. With such a modified drain pipe that already incorporates UV-C LED module(s) 30 it is not necessary to form openings or holes 34 by an installer and no silicone waterproofing 42 needs to be applied by the installer as the module is already integrated into the drain pipe with a suitable water proof seal.

The invention also includes the method of converting a conventional or typical drain pipe to disinfect the interior surface thereof by first forming a hole or aperture in a wall of the drain pipe. The disinfecting device including the UV-C LED module is positioned to register the module to be aligned with the hole or aperture 34 formed in the drain pipe to enable UV-C light to be transmitted through the hole or aperture. The resulting configuration is made waterproof by adding a seal to secure the module to the drain pipe to enable UV-C light to irradiate the drain pipe in the surface while creating a water tight seal to prevent fluid from escaping from the drain pipe. A plurality of spaced holes or apertures may be formed in the drain pipe and a plurality of modules can be sealingly secured thereto each in registration with an associated hole or aperture. When two or more holes and modules are used they are linearly and angularly spaced from each other along the length direction of the drain pipe in order to enhance or maximize the drain area of the drain pipe to UV-C radiation.

The foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

The invention claimed is:

1. A disinfecting device for disinfecting the interior of a drain pipe leading from a drain inlet of a sink basin mounted on a wall to a U-shaped trap beneath the sink basin comprising a drain pipe section below or downstream of the sink drain inlet provided with a hole or aperture between the sink drain inlet and the U-shaped trap; a UV-C LED module provided with a transparent medium through which UV-C light can be transmitted; means for sealingly attaching said module to the drain pipe section for creating a water tight seal between the drain pipe and said module and for registering said transparent medium with the hole in the drain pipe section to transmit UV-C light through said transparent medium into the interior of the drain pipe section to irradiate the interior of the drain pipe section and airborne pathogens contained therein with UV-C light proximate to said drain inlet; and control means for selectively energizing said module such that said module is de-energized at least when water is flowing through the drain pine section, whereby activation of the UV-C module controls the time periods during which pathogens are destroyed within said drain pipe section proximate to said drain inlet to inhibit pathogens from entry into the sink basin.

2. A drain disinfecting device as defined in claim 1, wherein said transparent medium is formed of glass or other UV-C transmissive lens.

3. A drain disinfecting device as defined in claim 1, wherein said transparent medium is formed of quartz.

4. A drain disinfecting device as defined in claim 1, wherein said sealing means comprises a silicone waterproofing seal at an interface between said hole or aperture and said module.

5. A drain disinfecting device as defined in claim 1, wherein said control means is housed within an enclosure and further comprising a conduit containing electrical conductors extending between said enclosure and said module.

6. A drain disinfecting device as defined in claim 1, wherein a plurality of modules are provided for attachment to the drain pipe in spaced relationship from each other for irradiating different inner surface portions of the drain pipe through associated holes or apertures in the drain pipe.

7. A drain disinfecting device as defined in claim 1, wherein said control means includes a motion sensor for de-energizing said module when motion is detected in the vicinity of the drain pipe.

8. A modified drain pipe for use between a sink basin and a trap comprising a section of a drain pipe leading from a drain inlet of a sink basin to a U-shaped trap beneath the sink basin; a drain disinfecting device for disinfecting the interior of said drain pipe section and airborne pathogens within said drain pipe section leading from a drain inlet of a sink basin mounted on a wall to a U-shaped trap beneath the sink basin wall through a hole or aperture in the drain pipe section, said disinfecting device comprising a UV-C LED module provided with a transparent medium through which UV-C light can be transmitted; means for sealingly attaching said module to the drain pipe section at said hole or aperture for creating a water tight seal between the drain pipe section and said module; and means for selectively energizing said module and for transmitting UV-C light through said transparent medium into the interior of said drain pipe section to irradiate the interior of the drain pipe section with UV-C light and airborne pathogens contained therein, said module being de-energized at least when water flows within said drain pipe section.

9. A modified drain pipe as defined in claim 8, wherein a plurality of modules are provided on said drain pipe.

10. A modified drain pipe as defined in claim 8, wherein said means for selectively energizing said module includes a programmable controller.

11. A method of converting a drain pipe to disinfect the interior space of a section of the drain pipe leading from a drain inlet of a sink basin mounted on a wall to a U-shaped trap beneath the sink basin comprising the steps of forming a hole or aperture in a wall of the drain pipe section; registering a drain disinfecting device comprising a UV-C LED module with said hole or aperture in the drain pipe section: energizing said UV-C LED module to enable UV-C light to be transmitted into the drain pipe section through the hole or aperture proximate to the drain inlet; sealingly securing said module to the drain pipe to enable UV-SC light to irradiate the interior of the drain pipe section and airborne pathogens contained therein while creating a water tight seal to prevent fluid from escaping from the drain pipe; and de-energizing said UV-C LED module at least when water flows within said drain pipe section, whereby the UV-C light controls the time periods during which pathogens are destroyed within said drain pipe section proximate to said drain inlet to inhibit pathogens from entry from said drain pipe section into the sink basin.

12. A method of converting a drain pipe as defined in claim 11, wherein said hole or aperture is formed by drilling a hole in the wall of the drain pipe.

13. A method of converting a drain pipe as defined in claim 11, wherein said module is secured to the drain pipe by applying an adhesive seal along an interface of said module and said hole or aperture.

14. A method of converting a drain pipe as defined in claim 11, wherein a plurality of spaced holes or apertures are formed in the drain pipe and each module is sealingly secured to an associated hole or aperture.

15. A method of converting a drain pipe as defined in claim 14, wherein said holes or apertures are both linearly and angularly spaced from each other along length direction of the drain pipe.

16. A drain disinfecting device as defined in claim 1, wherein said hole or aperture is located proximate to the drain inlet.

17. A modified drain pipe as defined in claim 8, wherein said hole or aperture is located proximate to the drain inlet.

18. A modified drain pipe as defined in claim 8, wherein said control means includes a motion sensor.

\* \* \* \* \*